United States Patent [19]

Lorenzetti

[11] Patent Number: 4,672,720
[45] Date of Patent: Jun. 16, 1987

[54] FASTENING APPARATUS

[75] Inventor: Theodore V. Lorenzetti, Stoneham, Mass.

[73] Assignee: Corflex, Inc., Winchester, Mass.

[21] Appl. No.: 846,031

[22] Filed: Mar. 31, 1986

[51] Int. Cl.⁴ .............................................. A44B 11/00
[52] U.S. Cl. ................................... 24/163 R; 24/165; 24/174; 128/91 A
[58] Field of Search ................. 24/163 R, 163 K, 165, 24/174, 265 R, 265 AL, 265 WS; 128/91 A

[56] References Cited

U.S. PATENT DOCUMENTS

| | | | |
|---|---|---|---|
| 363,033 | 5/1887 | Wheeler | 24/265 AL |
| 844,707 | 2/1907 | Barker | 24/174 |
| 1,284,695 | 11/1918 | Jendro | 24/174 |
| 2,112,742 | 3/1938 | Shindel | 24/265 R |
| 2,523,837 | 9/1950 | Luger | 128/91 A |
| 2,704,067 | 3/1955 | Moses | 128/91 A |
| 2,720,689 | 10/1955 | Maher | 24/163 R |
| 3,094,757 | 6/1963 | Blake | 24/265 R |
| 3,103,047 | 9/1963 | Wolf, Jr. | 24/165 |
| 3,747,171 | 7/1973 | Montague, Jr. | 24/265 WS |
| 4,398,306 | 8/1983 | Gooding | 24/265 R |

FOREIGN PATENT DOCUMENTS 1408418 7/1965 France ............................ 24/163 R Primary Examiner—Victor N. Sakran

[57] ABSTRACT

A fastener for bi-valve casts splints and other devices is disclosed which permits ease of use, change-ability of straps, reliability, convenience and detachability, that is, which permits repetitive attachment, removal and re-attachment. The fastener includes a base, attached to the device, a buckle universal mounted and detachably connected to the base, and a strap coupled to the buckle at one end and adapted to wrap the device and engage the buckle at its other end to secure the devices while preventing migration and rotation of the device from the original intended position.

1 Claim, 8 Drawing Figures

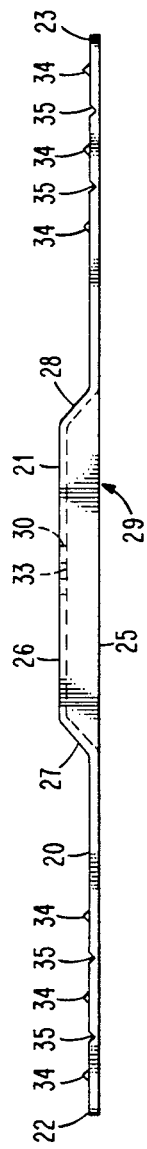
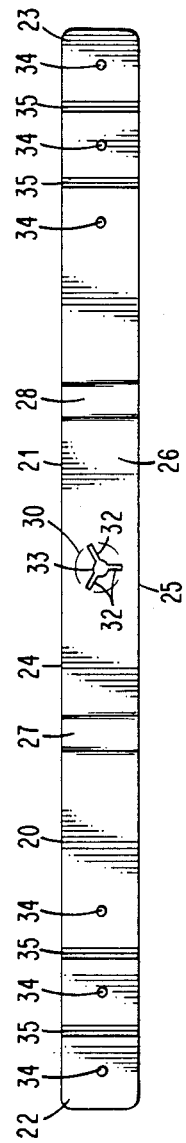
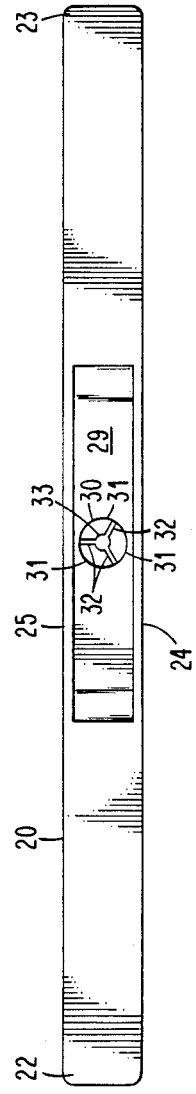

4,672,720

FASTENING APPARATUS

BACKGROUND OF INVENTION

1. Field of the Invention

This invention relates to fasteners and belts and, more particularly, to means for detachably securing orthopedic devices, such as, casts, splints, fracture braces and the like.

2. Description of the Prior Art

In the past, many types of fasteners, such as ties, belts, bands, straps, clasps, buckles, rivets, hooks and adhesive products, such as tapes, and combinations thereof have been used to detachably connect and/or secure various items. Certain items, such as boxes and cartons need means for temporarily joining or detachably connecting one portion of the box or carton to another portion of the box or carton, respectively.

In the medical field, some orthopedic items such as casts, splints, fracture braces and bi-valve casts may utilize or in some cases, necessarily require, means for temporarily or detachably securing said items. As these orthopedic devices may be made from various materials, such as, plaster and fiberglass, a reliable fastener suitable for use with various materials is desirable.

Many of these fastening means or securing devices were costly, complicated, not reuseable, not interchangeable, unreliable and/or inconvenient. Especially in the medical field, where ease of use, convenience, durability and replaceability are important, such prior devices were not totally adequate. Further, in certain orthopedic devices such as bi-valve casts, splits and the like, the device is intended to be temporarily secured or detachably coupled to the patient for a period of time. That is, the device is secured. Later, the device is removed. For example, the fastener is detached and the unsecured device is removed. At a later time, the device is once again attached to the patient. This sequence of attach, remove, re-attach may be repeated many times. Each time the device is attached, it is preferred that the device be secured in the same position as when originally formed. This situation of temporary use, detachable coupling and securing in the same position may be encountered by cerebral palsy patients, muscular dystrophy patients and others. Prior art fasteners, however, had a tendency to break during repetitive attach-detach procedures, which sometimes required the formation of an entirely new orthopedic device. In addition, prior art fasteners had a tendency to migrate, i.e. move from the intended position, slip, stretch and the like, or cause the device to migrate and/or rotate so as to be inconvenient, unreliable and not effective.

Accordingly, there is a need to provide a simple, inexpensive, reliable, easy to use and effective fastener for detachably connecting or temporarily securing items, such as orthopedic devices

SUMMARY OF THE INVENTION

In accordance with the invention, a fastener is provided which overcomes the difficulties of the prior art fasteners by means of an adjustable fixedly-detachable band.

Specifically, the fastener or securing device according to this invention comprises an adjustable band or belt member. The band or belt member is detachably fixed, at one end, to a first item and, at its other end it is detachably clasped or connected to detachably secure, a second item to the first item, or a removable portion of the first item to the other portion of the first item.

More specifically, an embodiment of this invention includes a clasping member which is detachably secured to an item. A strap is coupled at one end to the clasping member for; spanning an item to be secured or encircling the item to be fastened, and the other end of the strap is adjustably coupled to a second clasping member or another portion of the clasping member, respectively.

More specifically, in a further embodiment, the apparatus of this invention includes a base member which is fixedly secured within one portion of an orthopedic device, such as, a bi-valve cast. A buckle is detachably coupled to the base member and adapted to be rotatably adjustable to the proper orientation. In addition, a strap is coupled to one end of the buckle and adapted to encircle the cast and to adjustably couple to the other end of the buckle. The strap may be detached and reattached to the buckle as required.

The various features of novelty which characterize the invention are pointed out with particularity in the claims annexed to and forming a part of this specification. For a better understanding of the invention, its operating advantages and specific objects attained by its use, reference should be had to the accompanying drawings and descriptive matter in which there is illustrated and described a preferred embodiment of the invention.

BRIEF DESCRIPTION OF THE DRAWINGS

FIGS. 2, 3 and 4 are side, top and bottom views of the base member of the apparatus.

DETAILED DESCRIPTION OF THE PREFERRED EMBODIMENT

For a more complete appreciation of the invention, attention is invited to the following description of the preferred embodiment of the invention as shown in the attached drawings.

Figure 1:
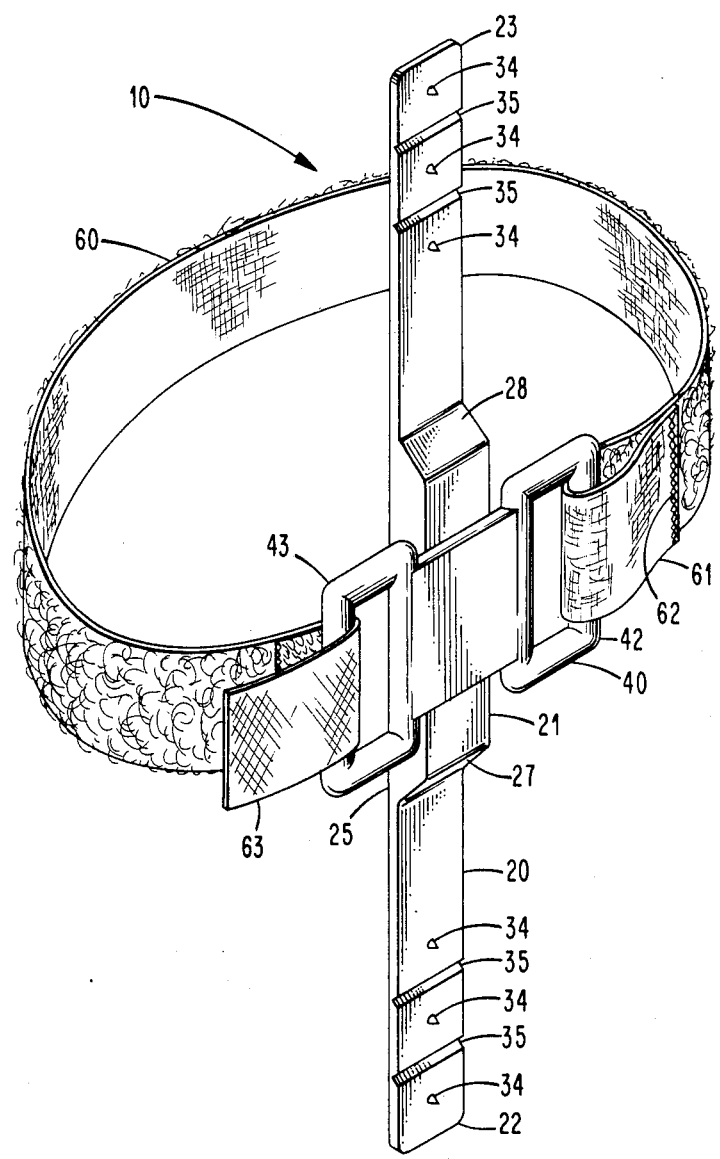
FIG. 1 is a perspective view of the apparatus.

Referring to FIG. 1, apparatus or fastener 10 of this invention is shown in its preferred embodiment. The apparatus 10 comprises a mounting plate or base member 20 (hereinafter called a "base"), a buckle or clasp 40 (hereinafter called a "buckle") coupled to the base through a universal mounting clasp or detachable connector as further described herein. The apparatus 10 further comprises a belt or strap 60 (hereinafter called a "strap") coupled at one end to the buckle 40 and detachably and adjustably coupled at its other end to the buckle 40 as more particularly pointed out herein below.

As illustrated more clearly in FIGS. 2, 3 and 4, the base 20 comprises a center portion 21 and two oppositely extending end portions 22, 23. The center portion 21 is formed of two oppositely rising elevated side wall surfaces 24, 25, a top surface 26 and oppositely rising angular surfaces 27, 28. The top surface 26 may be long and narrow as shown, or other shapes as appropriate for the device to be fastened. The surfaces 24, 25, 26, 27 and 28 define a hollow 29 more fully explained below. The base 20, and more specifically, the center portion 21 further comprise a connecting member 30 of the universal mounting clasp. In the preferred embodiment of the apparatus 10, the connecting member 30 is formed in the surface 26 of separate arcuate sections or segments 31 whose radially extending edges 32 allow or permit the segments 31 to flex bend or deflect in response to an applied force as further described. The segments 31 further define a central region or hole 33 which acts with the segments 31 to removably or detachably connect the apparatus 10 as more fully described herein.

The end portions 22, 23 of the base 20 are long flat flexible bands for mounting the base 20, for example within a bi-valve cast. The end portions 22, 23 are formed with a plurality of upwardly extending prongs 34 for assisting in the mounting of the base 20 within a bi-valve cast, for example, and holding the base 20 fixedly therein preventing migration and/or rotations of the base 20. In addition, the base 20 further includes a plurality of transverse notches 35 which allow the end portions 22, 23 to be trimmed to a smaller size by, e.g. flexure of the end portions 22, 23 breaking them off at the respective notches 35. Trimming of the end portions 22, 23 allows one base 20 to be suitably sized downwardly as needed for devices of different sizes.

Figure 5:
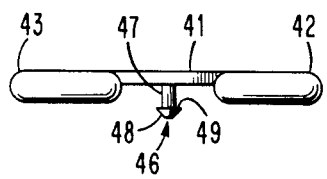
FIGS. 5, 6 and 7 are side, top and bottom views of the buckle member of the apparatus.
Figure 6:
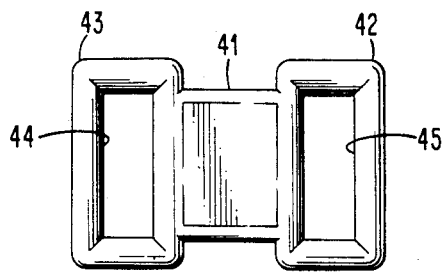
Figure 7:
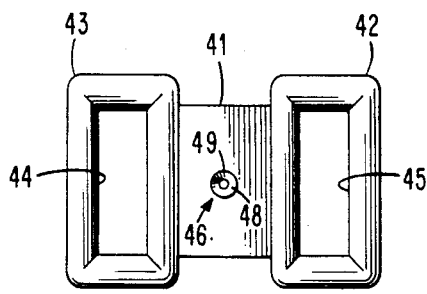

Now referring to FIGS. 5, 6 and 7, the buckle 40 comprises a central region 41 and oppositely extending and regions 42, 43 which in the preferred embodiment loop members 44, 45 for engaging the strap 60 as more fully described herein. The buckle 40 further comprises a cylindrically shaped rod or coupling member 46 for removably engaging or connecting the buckle 40 to the base 20 via the connecting member 30. In the preferred embodiment of the apparatus 10, the coupling member 46 as shown in FIGS. 5 and 7 is formed of a body portion 47 which extends downwardly from the plane of the buckle and which terminates in a conically shaped head 48. The circular base 49 of the head 48 is of larger diameter than the body portion 47 thereby allowing the coupling member 46 to engage the segments 31, when extended through the connecting member 30, and thereby resist removal. In the preferred embodiment of the invention, the diameter of the body portion 47 is of substantially the same diameter of the hole 33 in the connecting member 30. It is readily observed that other shaped coupling members may be utilized to engage or cooperate with the connecting member 30 or other suitably shaped member to form the universal-detachable connector described.

The strap 60, as shown in FIG. 1, is coupled to the loop member 44. In the preferred embodiment of this invention, one end 61, of the strap 60 is looped around and through the loop member 44 and stitched to itself at 62, although it will be readily observed that other methods of connecting one end of the strap 60 to the loop member 44 are available. The other end 63 of the strap is removably attachable to the loop member 43. In the preferred embodiment of the invention, as shown, the strap 60 includes the multiple hook-loop type fastening means commercially known as a pressure sensitive fastener. For example, a portion of end 63 includes the "hook" like portion of the pressure sensitive fastener; whereas, the remainder of the strap 60 includes the "loop" like fibers of the pressure sensitive fastener cooperable with the "hook" like portion. It is readily apparent that the strap 60 may be looped around an object and the end 63 connected through the loop member 43 to the strap 60 via the pressure sensitive fastener.

Figure 8:
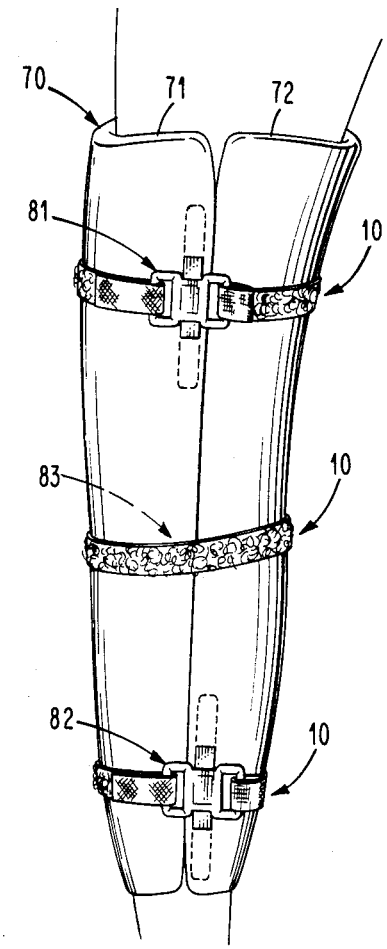
FIG. 8 is an illustration of a bi-valve cast being worn by a user showing the apparatus detachably securing the cast to the user.

The preferred embodiment of the apparatus 10 is illustrated in FIG. 8 as providing a method to secure an orthopedic device known as a bi-valve cast 70. In this illustration, three units of the apparatus 10 are used to secure the bi-valve cast 70. Although other methods of securing the cast may be used, FIG. 8 illustrates one method readily apparent and understood by those skilled or knowledgeable in this art. Namely, one fastener 10, for this illustration labeled 81, is fastened to one portion 71 of cast 70. In like manner, another fastener 10, labeled as 82 for ease of understanding of this FIG. 8, is fastened to the other half 72 of the cast. A third fastener 83 is fastened between fasteners 81 and 82 but on the opposite side of the cast. The orientation of the fasteners 10 as shown in FIG. 8 are but one of many positions intentionally arranged to prevent rotation and migration of the cast and for ease of use.

As further illustrated in FIG. 8, the apparatus 10 of this invention is both fixedly and removably attached to the cast 70.

Specifically, the base 20 is fixedly attached to the cast by being set in the cast during its formation. The end portion 22, 23, shown is dotted line in the figure are covered by the upper surface layers (e.g. plaster or fiberglass) of the cast and the detented notches 35 and the prongs 34 aid in fixing the position of the base 20 by grabbing or attaching to the cast layers. During this formation stage the doctor may adjust the size of the base 20 by breaking off portions at the notches. As will be recognized now, the raised center portion 21 extends about the surface of the cast thereby exposing the connecting member 30 whereas the end portions conform to the cast shape. After the cast is formed, the physician will determine which size buckle 40 and strap 60 is appropriate for the instant cast, as buckle size is readily interchangeable via the connecting member 30 and the coupling member 46. Specifically, once the buckle is chosen the coupling member 46 is pushed into, and through the segments 31 or "connected to" the connecting member 30. The reasons for the raised center portion 21 and the structural side walls 24, 25 are now readily apparent; to give strength to the connecting member and center portion, to displace the connecting member 46 from the cast itself during the coupling to the base 20 and provide clearance for the strap from the cast. Although other universal-detachable connecting means for readily attaching while permitting removement and later attachment, as well as, rotation of the buckle to the base are possible, the preferred embodiment has been found useful and easy to use for both patient and doctor. In addition, many materials for the base and buckle may be used, although polyethylene is preferred.

After the buckle 40 is coupled to the base 20, the strap 60 is wrapped about or encircles the cast 70, adjusted to the appropriate length and reattached to the other loop member of the buckle to secure the cast. In this preferred embodiment, the end of the strap is inserted through the loop member and attached, via the pressure sensitive fastener, to itself. In this manner, the apparatus of this invention easily and readily secures the cast.

In accordance with this invention, the patient may readily remove the cast by merely disengaging the strap 60. In like manner, the patient may secure the cast again by wrapping the end of the strap around cast inserting through the loop member of the buckle and fastening. Further, as time has a tendency to wear and/or dirty the strap, the easily removable buckle and the universal-detachable connector or clasp mounting permit attachment of a new buckle to the base, i.e. the cast.

In accordance with the apparatus 10 of this invention, a fastener is provided which overcomes the difficulties, the cost, the inconvenience and non-reusability of many types of fasteners. Further, the fastener of this invention secures the cast while preventing migration and rotation.

While the invention has been described in its preferred embodiment, it is to be understood that the words which have been used are words of description rather than limitation and that changes within the purview of the appended claims may be made without departing from the true scope and spirit of the inventions in its broader aspects.

What is claimed is:

1. A fastener for a bi-valve cast comprising, a base, having oppositely extending flexible ends, each of said ends having means for fixedly securing the base to a separate portion of the cast, a buckle, the buckle having a coupling means for detachably securing the buckle to the central portion of the base, and a strap, for encircling the cast, coupled at one end to one end of the buckle and adjustably connected at its other end to the opposite end of the buckle, the coupling means including a detachable, rotatable clasp, for coupling and rotatably orientating the buckle and the strap to the base such that the buckle and the strap are rotatably adjustable to the proper orientation to fasten the cast.

* * * * *